United States Patent [19]

Billings et al.

[11] Patent Number: 5,395,363
[45] Date of Patent: Mar. 7, 1995

[54] DIATHERMY COAGULATION AND ABLATION APPARATUS AND METHOD

[75] Inventors: R. Gail Billings, Hollday; Christopher A. Cutler, Centerville; David A. Bush, Bountiful, all of Utah

[73] Assignee: Utah Medical Products, Midvale, Utah

[21] Appl. No.: 84,861

[22] Filed: Jun. 29, 1993

[51] Int. Cl.[6] ............................................. A61B 17/39
[52] U.S. Cl. ........................................ 606/41; 606/45; 606/48; 606/50
[58] Field of Search ...................... 607/147–150, 607/115, 116; 606/41, 45, 48–50, 29; 128/642

[56] References Cited

U.S. PATENT DOCUMENTS

| 642,849 | 2/1900 | Otto | 607/147 |
|---|---|---|---|
| 4,095,601 | 6/1978 | Aufrank et al. | 607/147 |
| 4,314,559 | 2/1982 | Allen | 606/45 |
| 4,532,924 | 8/1985 | Auth et al. | 606/50 |
| 4,765,331 | 8/1988 | Petruzzi et al. | 606/50 |
| 4,917,082 | 4/1990 | Grossi et al. | 606/49 |

*Primary Examiner*—Stephen C. Pellegrino
*Assistant Examiner*—Michael Peffley
*Attorney, Agent, or Firm*—Madson & Metcalf

[57] ABSTRACT

An apparatus for facilitating diathermy coagulation or ablation of tissue by the application of an electrical current to tissue is connectable to an electrosurgical generator having an active lead and a return lead, and has both monopolar and bipolar embodiments. A preferred monopolar embodiment includes a shaft and a knurled active electrode rotatably secured to the shaft. A preferred bipolar embodiment includes a knurled active electrode separated by an insulator from a return electrode, with the active and return electrodes rotatably secured to a shaft by axles. The shafts may be Y-shaped, crook-shaped, or otherwise. The active electrodes have a plurality of discrete electrically conductive discharge points for applying the electrical current to a plurality of discrete tissue locations, the discharge points preferably being formed as knurl peaks. The active electrode may be formed of a stick-resistant metal, may be covered in part or whole by a nonstick coating, and may be formed in a variety of shapes and sizes.

29 Claims, 4 Drawing Sheets

DIATHERMY COAGULATION AND ABLATION APPARATUS AND METHOD

FIELD OF THE INVENTION

The present invention relates to an apparatus and method for performing diathermy to achieve coagulation or ablation, and more particularly to an apparatus and method using high frequency electric current to coagulate or ablate tissue which employ a plurality of discrete points for more evenly distributing the electric current over the tissue.

TECHNICAL BACKGROUND OF THE INVENTION

Surgery necessarily severs blood vessels, thereby releasing blood into the incision. Bleeding during surgery may cause several undesirable results. Blood covering critical areas of the patient's anatomy increases the risk of error and the time required for operations by obscuring the surgeon's field of vision. Additionally, blood loss may directly threaten the patient's life during the surgery, making transfusions necessary. However, transfused blood is drawn from a limited supply and may expose the patient to communicable diseases. Finally, compensating for blood loss also requires additional time and energy from both patient and medical facility during the patient's recuperation after surgery. Thus, the cessation of bleeding, known as hemostasis, is highly desirable.

Hemostasis is facilitated by coagulation, a process whereby blood is converted from a liquid to a solid state. Coagulation may be effected by passing an electric current through the body of the patient so that concentrated electrical energy heats the tissue in contact with the coagulation electrode. Thus, in monopolar electrosurgery a radio frequency current is passed from an active electrode, where the current is highly concentrated, through the patient to a dispersive electrode. The current is diffuse at the dispersive electrode, so coagulation occurs only near the active electrode. Various frequencies are used, but frequencies above 400 Khz are commonly employed.

Desiccation coagulation may be achieved by using a blunt active electrode and relatively low power. The power required varies with the conductivity of the tissue and the area of contact between the tissue and the active electrode, but voltages in the range from 200 V to 900 V are typical. The current raises tissue temperature enough to dry and shrink cells, denature protein, and promote clotting of blood.

Fulguration coagulation, by contrast, employs either a blunt or fine electrode and relatively high power, voltages in the range 900 V to 2000 V being typical. The active electrode is maintained at a small distance from the tissue so that sparks jump the gap from the active electrode to the tissue. At each point of the tissue contacted by a spark, the current density is quite high, so the tissue at the contact point is seared. However, the surface area seared by each spark is small, and the overall heat damage to the tissue is shallow. Fulguration usually provides good cosmetic results after healing.

If proper distribution of current is not maintained during coagulation, the overall heat damage to the patient may be excessive. Undesirable current concentration due to contact between the active electrode and the tissue is exacerbated by the tendency of some bare metal electrodes to stick to tissue. When an electrode sticks to tissue, much or all of the electrical current discharged from the electrode may pass through the same portion of the patient's body. The resulting burns may substantially increase the patient's healing period. In addition, of course, tissue is damaged when a sticking electrode is pulled away from the tissue.

Electrodes are also used to destroy undesirable tissue by electrothermal ablation. Ablation involves the thermal destruction of undesirable tissue. For instance, endometrial tissue proliferating outside the uterus in a woman's pelvic or abdominal cavity may impair fertility. An electrode carrying high frequency current can be passed over such tissues to destroy the abnormal cells. Ablation typically employs lower voltages and higher currents than electrosurgical coagulation. During ablation, unlike fulguration, sparking is unnecessary or even undesirable. As with coagulation, however, it is desirable during ablation to apply the current at evenly-distributed concentration points.

The term "diathermy" encompasses not only ablation and electrosurgical coagulation, but also certain medical procedures used in treating arthritis or rheumatism. As used herein, however, diathermy means the application of high frequency electrical current to tissue to perform coagulation, ablation, or both. Proper current distribution for diathermy requires that fulguration sparks or other current concentrations be distributed over a plurality of discrete tissue locations. Devices previously known, however, emit sparks from one electrical discharge point or non-uniformly over a region. Because each spark or point concentration coagulates or ablates only a small surface area, larger areas can be difficult to treat, even if the active electrode is moved slightly after each discharge. Maintaining a spark gap for fulguration is difficult because tissue surfaces requiring coagulation are not often planar, are often located within incisions that restrict the surgeon's freedom of movement, and may be difficult to view.

Advantageously, a proper current distribution may be maintained using the present invention simply by placing the active electrode against the tissue and rolling the active electrode along the tissue. As the active electrode rotates, successive pluralities of electrical discharge points situated on the rotating active electrode come into spark gap distance or contact with the tissue. The surgeon's task in maintaining a spark gap becomes the manageable one of maintaining contact between the active electrode and the tissue, rather than the difficult task of maintaining a consistent distance between the active electrode and the tissue or covering a large area with a few discharge points.

Prior art devices are also monopolar in nature. That is, the surgeon manipulates a small active electrode which emits current that travels through the patient to a large dispersive electrode, and thence back to the electrosurgical generator. The dispersive electrode, also denoted the return electrode or return lead, is conventionally large and fixed in place on the patient's leg or some other location permitting large surface area contact between the return lead and the patient.

A major drawback of such monopolar systems is that the electrical current entering the patient from the active electrode is not always constrained to exit the patient at the return lead. Accidental contacts between the surgeon and patient or between the patient and some conductive operating fixture such as a table may result in burns to patient or surgeon or both when the electrical current deviates from its preferred path back to the electrosurgical generator through the dispersive electrode.

Thus, it would be an advancement in the art to provide an active electrode capable of discharging electric current in a substantially uniform distribution.

It would also be an advancement in the art to provide an active electrode for diathermy that did not easily stick to tissue.

It would be a further advancement to provide a diathermy apparatus and method for uniformly and rapidly coagulating or ablating an area of tissue substantially larger than the area affected by any single spark.

It would be an additional advancement in the art to provide a bipolar diathermy apparatus and method in which the return electrode traveled along the patient's tissue in close physical and electrical proximity to the active electrode, thereby reducing the risk of burns by more tightly constraining the paths current may take.

Such a diathermy apparatus and method are disclosed and claimed herein.

BRIEF SUMMARY AND OBJECTS OF THE INVENTION

The apparatus of the present invention includes both monopolar and bipolar embodiments of an active electrode having a plurality of discrete electrical discharge points. This plurality of discrete points may be provided, for instance, by knurling the exterior surface of the active electrode. Knurls provide a plurality of distinct points for current discharge, facilitating evenly distributed current through the tissue.

Because the apparatus provides a plurality of electrical discharge points, tissue surface areas larger than the area affected by a single spark may be subjected to diathermy without moving the active electrode after each current discharge. Advantageously, this knurled surface may be utilized on active electrodes of various sizes and shapes, including surfaces of rotation such as cylinders or ovoids. Thus, one method taught by the present invention includes rolling the active electrode along the tissue to be treated. To prevent the electrode from sticking to the tissue, the electrode may be constructed of stick-resistant metallic materials, or portions of the electrode may be covered by a nonstick coating such as polytetrafluoroethylene, commonly known as TEFLON ®.

The active electrode may be rotatably or fixedly mounted on a variety of positioning means. For instance, the electrode could be rotatably secured to a shaft which is lightweight, sterile, and at least partially electrically insulated. An axle upon which the active electrode rotates may be oriented transversely or otherwise to the shaft. The shaft may be straight, Y-shaped, crooked in part, or otherwise shaped for convenient use of the active electrode by a physician for diathermy. It will be appreciated by one of skill in the art that gloves or other positioning means may also be employed to guide an active electrode.

The methods and apparatus of the present invention may be practiced with a monopolar electrosurgical generator connected electrically to a dispersive return electrode which is fixedly attached to a patient during treatment. Such dispersive electrodes are conventionally orders of magnitude larger than the active electrode employed.

Alternatively, a bipolar embodiment of the present invention may be used. In such a bipolar embodiment, the return electrode is approximately the same size as the active electrode, and is fixed in position relative to the active electrode, not relative to the patient.

Both bipolar and monopolar embodiments may be constructed of sterilizable materials. However, it is contemplated that disposable embodiments of the present invention will be commercially feasible. Disposable embodiments substantially reduce the risk of infection to patients and the potential hazards of insulation failure, short circuits, and other eventual results of repeated use.

In view of the foregoing, it is a primary object of the present invention to facilitate rapid and uniform diathermy by providing an active electrode having a plurality of discrete electrical discharge points capable of applying current to tissue.

It is also an object of the present invention to provide a bipolar diathermy apparatus and method which reduce the risks posed by stray electrical currents to physicians and their patients.

It is another object of the present invention to provide an active electrode that does not stick easily to tissue.

A further object of the present invention is to facilitate diathermy within a wide variety of incisions by providing lightweight active electrodes of varied geometry and size.

Still another object of the present invention is to provide an electrode that is disposable.

These and other features and objects of the present invention will become more fully apparent through the following description and appended claims taken in conjunction with the accompanying drawings.

BRIEF DESCRIPTION OF THE DRAWINGS

In order that the manner in which the above-recited and other advantages and objects of the invention are obtained, a more particular description of the invention summarized above will be rendered by reference to the appended drawings. Understanding that these drawings only provide data concerning typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Reference is now made to the figures wherein like parts are referred to by like numerals throughout. One preferred embodiment of the present invention, depicted in FIG. 1, is generally designated 10.

Figure 1:
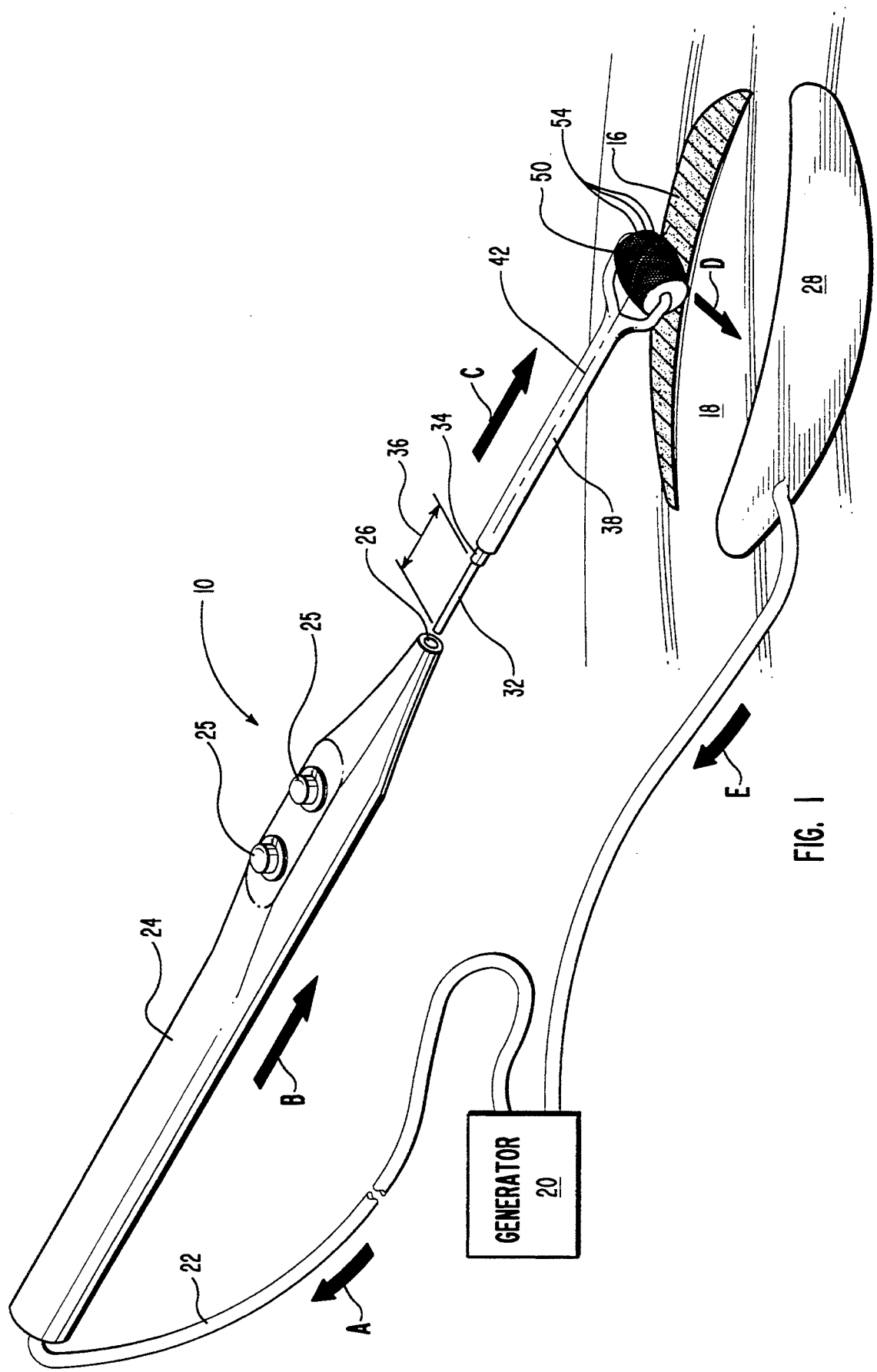
FIG. 1 is an exploded perspective view of one preferred embodiment of a monopolar diathermy apparatus near an area of tissue needing treatment.

FIG. 1 illustrates generally the flow of energy when a monopolar embodiment of the present invention is utilized. An electrosurgical generator 20 produces high frequency current that is transmitted in the direction of Arrow A through a power cord 22 to a handle 24. The handle 24 preferably comprises a conventional electrosurgical pencil, either with or without switches 25. Together with a shaft 38, the handle 24 and shaft 38 may comprise a positioning means for facilitating manipulation of the tool. It should be understood, however, that other forms of positioning means are contemplated and are intended to fall within the scope of this invention. For example, the positioning means may comprise a glove (not shown), the glove and shaft 38, or the shaft 38 connected directly to the power cord 22.

In the case of the handle 24 shown, electrical current from the power cord 22 flows through the handle 24 in the direction of Arrow B to a socket 26. When the apparatus 10 is in use, an active lead 32 fits inside the socket 26 and electrically engages the power cord 22. As indicated by Arrow C, electrical current flows from the active lead 32 generally along a longitudinal axis 42 of the insulated shaft 38 to an active electrode 50.

Figure 3:
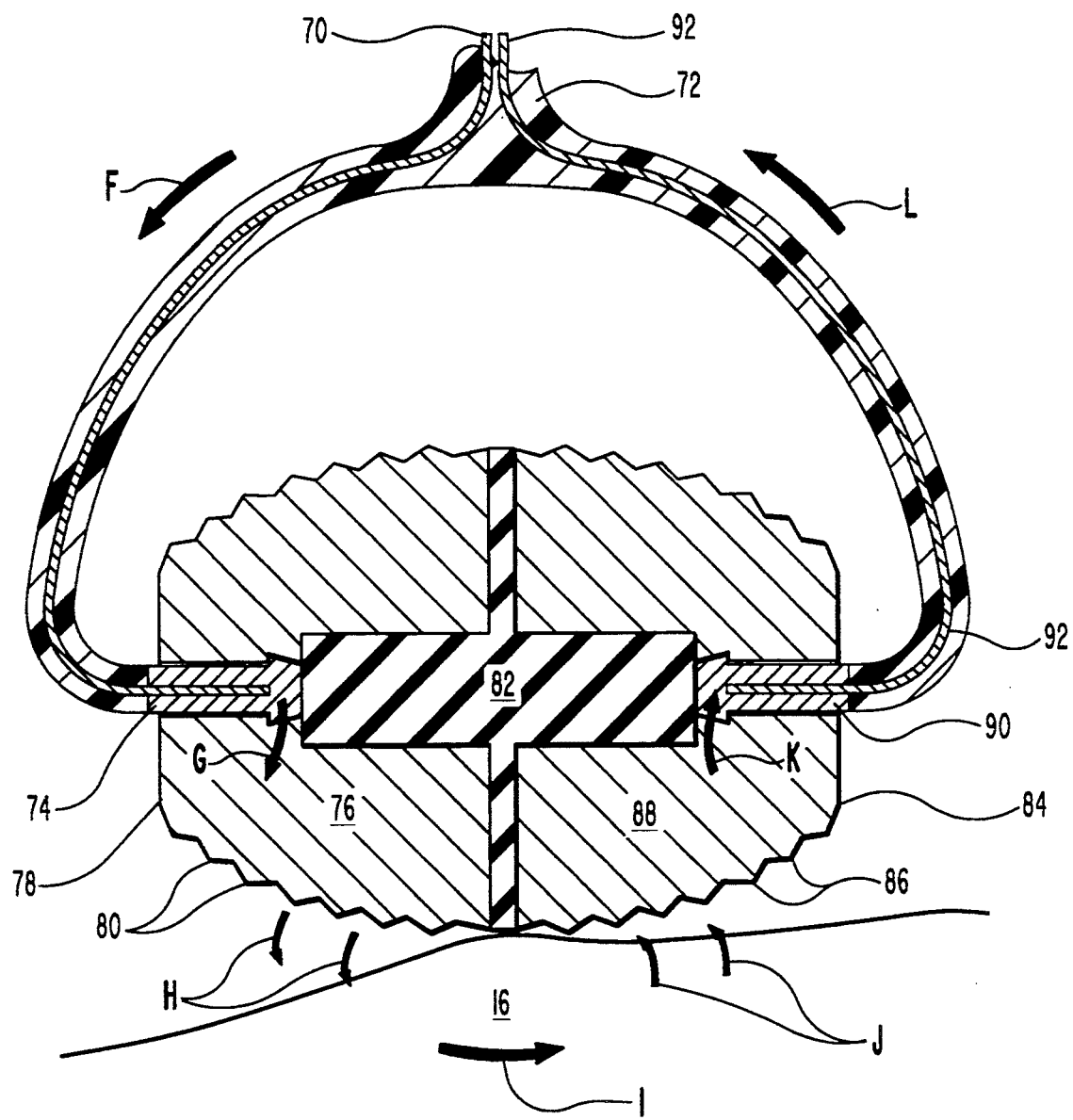
FIG. 3 is an enlarged cross-sectional view of a knurled bipolar embodiment of the active electrode of the present invention.

The shaft 38 shown in FIG. 1 is monopolar, having only one lead 32 electrically connectable to the power cord 22. Bipolar embodiments, such as depicted in FIG. 3, would necessarily have two leads, an active lead for receiving current from the electrosurgical generator and a return lead for returning current to the electrosurgical generator. Both the handle and the power cord would also contain a return lead in addition to an active lead.

Figure 4:
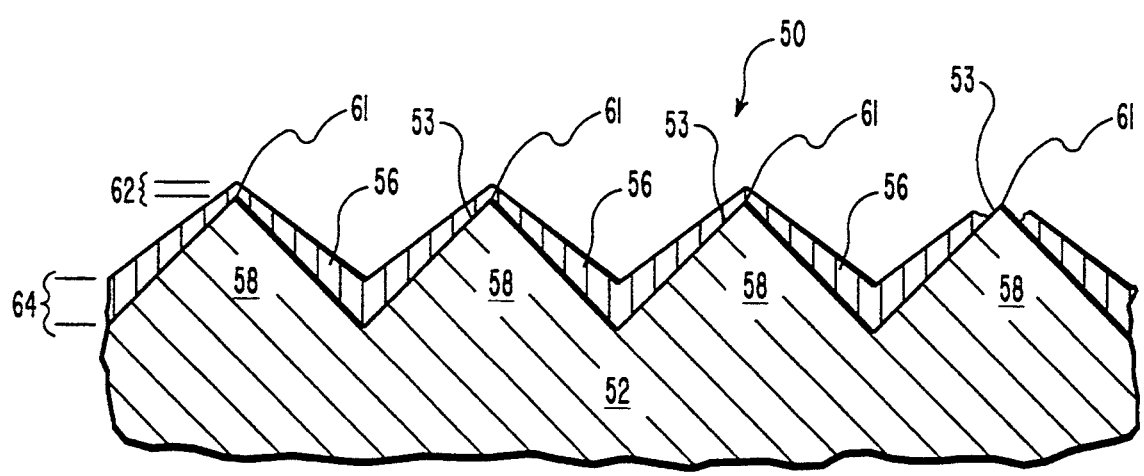
FIG. 4 is a partial cross-sectional view taken through the knurled surface shown in FIG. 2 to illustrate an application of nonstick coating over the knurled surface.

With reference to FIGS. 1 and 4, the active electrode 50 emits current from a plurality of discrete electrical discharge points 54 formed on its exterior surface 53 into a tissue 16 to be coagulated or ablated. The current travels generally in the direction of Arrow D through the patient toward a dispersive electrode 28 which is attached to another portion 18 of the patient's body. Unlike the active electrode 50, the dispersive electrode 28 has a large area of contact with the patient, so current density is low enough to prevent substantial harm to the tissue 18 near the dispersive electrode 28. Finally, the current travels in the direction of Arrow E from the dispersive electrode 28 back to the generator 20, thereby completing the circuit.

Most of the shaft 38 of the apparatus 10 is preferably insulated. The apparatus 10 may be constructed of materials capable of sterilization for reuse, or may be disposable. In either case, the shaft 38 is preferably constructed of lightweight materials to minimize the mass a surgeon must control. An annular recess 34 formed by thinner insulation near the exposed active lead 32 facilitates secure engagement of a desired length 36 of the shaft 38 inside the socket 26.

Figure 2:
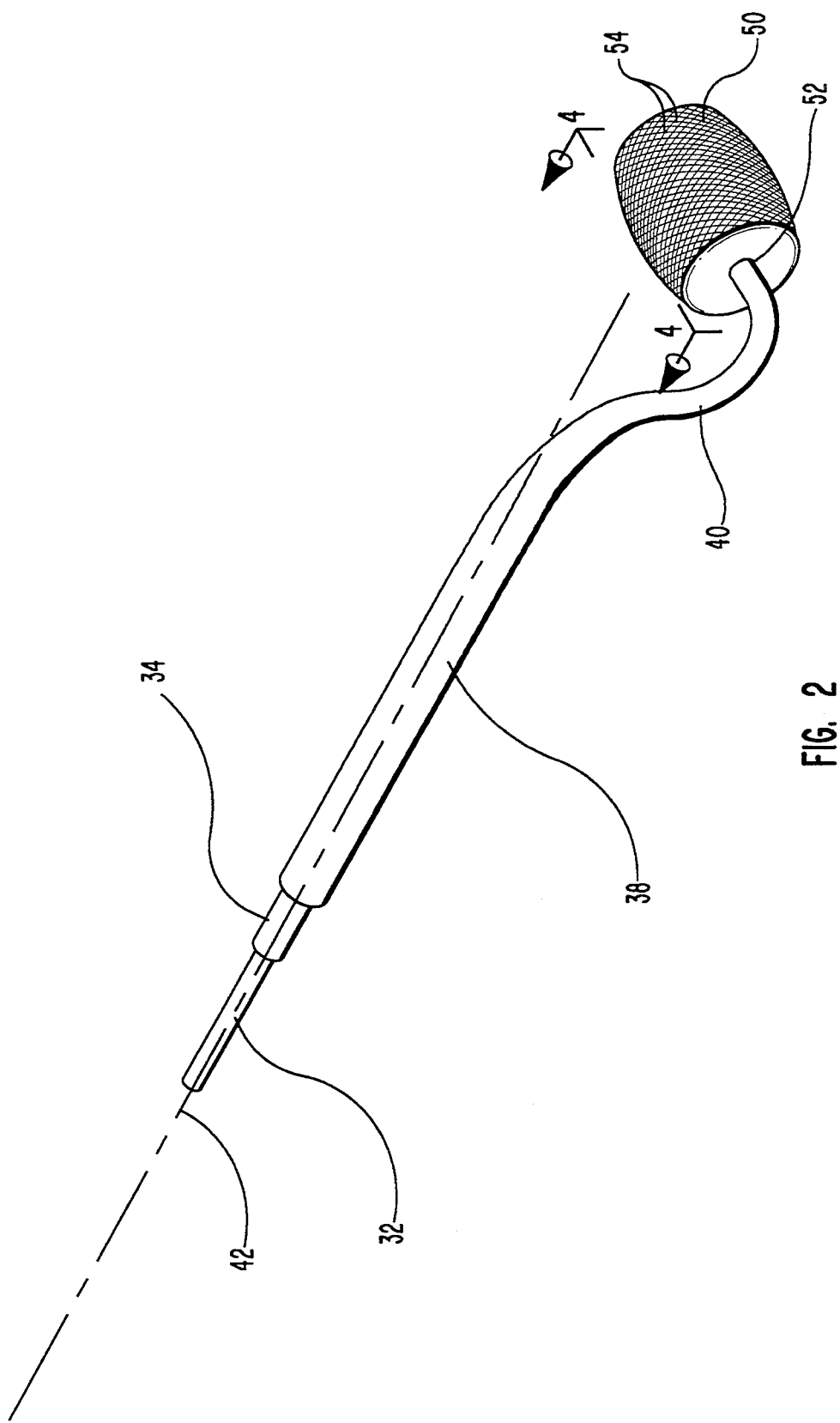
FIG. 2 is a perspective view of an alternative monopolar embodiment of the present invention which employs a crook-shaped shaft.

It will be appreciated that the shaft 38 may be shaped in a variety of ways to facilitate positioning by the surgeon. FIG. 1 shows a Y-shaped shaft 38, while FIG. 2 illustrates an alternative embodiment of the shaft 38 which has a crook-shaped portion 40. The dimensions of the active electrode 50, the electrical discharge points 54, the shaft 38, and other parts of the present invention may likewise be tailored to suit particular circumstances. Furthermore, the orientation of the active electrode 50 with respect to the longitudinal axis 42 of the shaft 38 may vary among a plurality of embodiments which are all encompassed by the claims set forth herein.

In the presently preferred embodiment shown in FIG. 1, the electrode 50 is rotatably secured to the shaft 38. Rotatable attachment permits the surgeon to roll the electrode 50 along the tissue 16 to be treated. Slight pressure of the electrode 50 against the tissue 16 provides sufficient friction to rotate the electrode 50 as the positioning means is manipulated to move the electrode 50 along the tissue 16. Thus, the electrical discharge points 54 need not stay in contact with the same region of tissue long enough to risk burns. Furthermore, successive pluralities of electrical discharge points 54 roll into spark gap range of the tissue 16 and into contact with the tissue 16 as the electrode 50 rotates. If the voltage created by the generator 20 is sufficient, sparks will be emitted from the discharge points 54 as they roll toward contact with the tissue 16. At some electrical voltage levels, depending on the tissue 16 being coagulated, desiccation and fulguration can therefore be achieved simultaneously using the electrode 50.

Those portions of the active electrode 50 which will contact the tissue 16 may be constructed to inhibit sticking. Sticking may be inhibited by constructing the active electrode of an appropriate metal, such as soft steel, stainless steel, brass, or a suitable alloy. Sticking may also be inhibited by covering a portion of the exterior surface 53 of the electrode 50 with a nonstick coating such as polytetrafluoroethylene, which is sold commercially under the trademark TEFLON®. Such a nonstick coating may be of substantially uniform thickness, or its thickness may be varied in a fashion that facilitates transmission of current from the metal active electrode 50 to the tissue 16.

FIG. 4 illustrates an application of a nonstick coating 56 to the exterior surface 53 of a core 52 of an active electrode 50. The coating decreases in thickness near several peaks 60 of knurls 58 on the exterior surface 53 of the electrode 50. Thus, the depth 62 of the coating 56 at a peak 60 is less than the depth 64 of the coating 56 between peaks 60. Such coated electrodes 50 could be used in the condition depicted, or could be "burned in" by applying a large voltage that causes perforations 61 that expose the peaks 60. Alternatively, peaks 60 could be exposed by sanding away portions of the coating 56, or by other methods.

FIG. 1 shows an embodiment of the active electrode 50 having a knurled exterior surface 53. One of skill in the art will appreciate that other means may also achieve a plurality of discrete electrical discharge points. Such other means are also intended to be within the scope of the present invention. For instance, knobs, bumps, or other protrusions may be employed. Discrete electrically conductive discharge points could also be defined merely by wrapping a perforated layer of insulation about a conductor. However, knurls, wire segments, or similar protrusions are presently preferred, because each such protrusion creates a voltage gradient and so discharges electrical energy from a predictable location, namely, the tip of the protrusion.

Both FIGS. 1 and 2 depict an ovoid active electrode 50, but cylinders, cones, or other shapes may also be fruitfully employed in embodying the present invention. Such shapes need not be restricted to surfaces of revolution. Although the presently preferred embodiment employs an active electrode which is rotatably secured to a shaft, the teachings of the present invention also include active electrodes which are fixed in position relative to a shaft.

Regardless of whether the active electrode 50 is rotatable, a spark gap permitting fulguration coagulation may be maintained by the surgeon so that the active electrode 50 does not physically contact the tissue 16 to be coagulated. The size of the gap depends on the voltage produced by the generator 20 and the conductivity of the tissue 16. However, an appropriate gap may be ascertained by the surgeon in each instance by placing the active electrode 50 several inches away from the tissue 16 and gradually closing this distance until sparks are emitted from the electrode 50.

The monopolar embodiment illustrated in FIG. 1 has one exposed active lead 32 which is electrically connectable to the power cord 22. However, bipolar embodiments of the present invention are also contemplated. Of course, bipolar embodiments require both an active lead and a return lead (not shown in FIG. 1), but many aspects of the present invention discussed in connection with a monopolar embodiment, such as the use of knurls or a crook-shaped shaft, may be used in connection with either monopolar or bipolar embodiments.

A presently preferred bipolar embodiment is shown in an enlarged cross section of an active electrode 78 and a return electrode 84 in FIG. 3. The flow of current is generally designated by Arrows F through L. An active lead 70 brings current from the electrosurgical generator through a Y-shaped insulated shaft 72 along the path indicated generally by Arrow F into an electrically conductive axle 74. As indicated by Arrow G, the current flows from the axle 74 into a core 76 of an active electrode 78. An insulator 82 electrically separates the active electrode 78 from a return electrode 84. Current may travel from the active electrode 78 around the insulator 82 to the return electrode 84 if a conductor sufficiently approaches the active electrode 78 and the return electrode 84. Of course, alternating current alternates its direction of travel, but it is convenient to label one electrode as "active" and the other as "return" while describing the present invention. Thus, if the active electrode 78 and the return electrode 84 sufficiently approach the tissue 16, current may travel from the active electrode 78 through the tissue 16 in the direction generally indicated by Arrows I and J to the return electrode 84.

In traveling from the active electrode 78 to the return electrode 84 shown in FIG. 3, current flows from a plurality of electrically conductive discharge points 80 to a plurality of discrete electrically conductive reception points 86. Current may therefore both enter and emerge from the tissue 16 at discrete locations. Advantageously, dispersed current may therefore cause coagulation or ablation both upon entering the tissue 16 and upon leaving the tissue 16.

From the electrically conductive reception points 86, current flows as indicated by Arrow K through a core 88 of the return electrode 84 to a return axle 90. From the return axle 90, the current flows as indicated by Arrow L along a return lead 92 back to the electrosurgical generator (not shown), thereby completing the circuit.

It should be appreciated that the apparatus and methods of the present invention are capable of being incorporated in the form of a variety of embodiments, only a few of which have been illustrated and described above. The invention may be embodied in other forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus connectable to an electrosurgical generator for facilitating diathermy of tissue with a radio frequency electrical current from the electrosurgical generator, comprising:

a core having an exterior surface;

a plurality of discrete radio frequency electrically conductive discharge points for applying the radio frequency electrical current to a plurality of discrete tissue locations, said radio frequency electrically conductive discharge points disposed on protrusions on said exterior surface of said core, said protrusions comprising a plurality of knurls disposed on said exterior surface of said core, each of said knurls terminating in at least one of said radio frequency electrically conductive discharge points; and a positioning means disposed adjacent to said core for positioning said radio frequency electrically conductive discharge points relative to the tissue to facilitate diathermy, said positioning means comprising an active lead which is electrically connected to said radio frequency electrically conductive discharge points and which is electrically connectable to the electrosurgical generator.

2. The apparatus of claim 1, wherein at least a portion of said exterior surface of said core is substantially ovoid in shape.

3. The apparatus of claim 1, wherein at least a portion of said exterior surface of said core is substantially cylindrical in shape.

4. The apparatus of claim 1, wherein said core is rotatably secured to said positioning means such that successive pluralities of said radio frequency electrically conductive discharge points rotate into electrical contact with the tissue if an initial plurality of said radio frequency electrically conductive discharge points is placed in frictional engagement with the tissue and said positioning means is manipulated to roll said core along the tissue.

5. The apparatus of claim 1, wherein said core is rotatably secured to said positioning means, and said apparatus further comprises an insulating layer that covers at least a portion of said exterior surface of said core, said insulating layer having perforations aligned with at least a portion of said radio frequency electrically conductive discharge points.

6. The apparatus of claim 1, wherein said radio frequency electrically conductive discharge points comprise a metallic material substantially resistant to sticking to the tissue during diathermy.

7. The apparatus of claim 1, wherein at least a portion of said positioning means is electrically insulated from said radio frequency electrically conductive discharge points, such that a physician may manipulate said positioning means by hand.

8. The apparatus of claim 1, wherein said positioning means comprises:

a shaft having a longitudinal axis; and an axle connected to said shaft and angled away from the longitudinal axis of said shaft, said core being rotatably secured upon said axle.

9. The apparatus of claim 8, wherein said axle is connected to a crook-shaped portion of said shaft.

10. The apparatus of claim 8, wherein said axle is connected to a Y-shaped portion of said shaft.

11. The apparatus of claim 8, wherein said axle is disposed substantially transverse to the longitudinal axis of said shaft.

12. The apparatus of claim 8, wherein at least a portion of said axle is electrically conductive and is disposed electrically between the electrosurgical generator and said radio frequency electrically conductive discharge points, for conducting radio frequency electrical current from the electrosurgical generator to said radio frequency electrically conductive discharge points.

13. The apparatus of claim 1, further comprising a nonstick coating that covers at least a portion of said exterior surface of said core.

14. The apparatus of claim 13, wherein said nonstick coating comprises polytetrafluoroethylene.

15. The apparatus of claim 13, wherein said nonstick coating decreases in thickness near said radio frequency electrically conductive discharge points.

16. The apparatus of claim 1, wherein said core further comprises an insulator and an electrically conductive reception member for receiving and returning to the electrosurgical generator at least a portion of the radio frequency electrical current discharged from said radio frequency electrically conductive discharge points, said insulator being disposed between said radio frequency electrically conductive discharge points and said electrically conductive reception point, and said electrically conductive reception point being electrically connected to the electrosurgical generator.

17. An apparatus connectable to an electrosurgical generator for facilitating coagulation and ablation of tissue by the application of a radio frequency electrical current from the electrosurgical generator to the tissue, comprising:
- a shaft having a longitudinal axis and comprising an active lead which is electrically connectable to the electrosurgical generator;
- an axle connected to said shaft and angled away from the longitudinal axis of said shaft;
- a core having an exterior surface, said core rotatably secured to said axle; and
- a plurality of discrete radio frequency electrically conductive discharge points for applying the radio frequency electrical current to a plurality of discrete tissue locations, said radio frequency electrically conductive discharge points disposed on protrusions on said exterior surface of said core and electrically connected to said active lead for connection to the electrosurgical generator.

18. The apparatus of claim 17, wherein said protrusions comprise a plurality of knurls disposed on said exterior surface of said core, each of said knurls terminating in at least one of said radio frequency electrically conductive discharge points.

19. The apparatus of claim 17, further comprising a nonstick coating that covers at least a portion of said exterior surface of said core.

20. A bipolar apparatus connectable to an electrosurgical generator having an active lead and a return lead, the bipolar apparatus for facilitating diathermy by the application to tissue of a radio frequency electrical current emanating from the active lead of the electrosurgical generator, the bipolar apparatus comprising:
- a core having an exterior surface, comprising:
  - a plurality of discrete radio frequency electrically conductive discharge points for applying the radio frequency electrical current to a plurality of discrete tissue locations, said radio frequency electrically conductive discharge points disposed on protrusions on said exterior surface and electrically connectable to the active lead of the electrosurgical generator;
  - an electrically conductive reception member for receiving and returning at least a portion of the radio frequency electrical current discharged from said radio frequency electrically conductive discharge points, said electrically conductive reception member disposed on said exterior surface and electrically connected to the return lead; and
  - an insulator disposed between and electrically insulating said radio frequency electrically conductive discharge points from said electrically conductive reception member; and
- a positioning means disposed adjacent to said core, for positioning said exterior surface of said core relative to the tissue, said positioning means comprising a positioning means active lead which is electrically connected to said radio frequency electrically conductive discharge points and which is electrically connectable to the active lead of the electrosurgical generator, said core being rotatably secured to said positioning means such that successive pluralities of said radio frequency electrically conductive discharge points rotate into electrical contact with the tissue if an initial plurality of said radio frequency electrically conductive discharge points is placed in frictional engagement with the tissue and said positioning means is manipulated to roll said core along the tissue.

21. The bipolar apparatus of claim 20, wherein said positioning means comprises:
- a shaft having a longitudinal axis; and
- an axle connected to said shaft and angled away from the longitudinal axis of said shaft, said core being rotatably secured upon said axle.

22. The bipolar apparatus of claim 20, wherein said protrusions comprise a plurality of knurls disposed on said exterior surface of said core, each of said knurls terminating in at least one of said radio frequency electrically conductive discharge points.

23. The bipolar apparatus of claim 20, wherein said electrically conductive reception member comprises a plurality of discrete electrically conductive reception points, for receiving radio frequency electrical current from a plurality of discrete tissue locations and returning the radio frequency electrical current to the return lead.

24. The bipolar apparatus of claim 20, further comprising a nonstick coating that covers at least a portion of said exterior surface of said core.

25. A bipolar apparatus connectable to an electrosurgical generator having an active lead and a return lead, the bipolar apparatus for facilitating coagulation or ablation of tissue by the application to tissue of a radio frequency electrical current emanating from the active lead of the electrosurgical generator, the bipolar apparatus comprising:
- a shaft having a longitudinal axis;
- an axle connected to said shaft and angled away from the longitudinal axis of said shaft;

a core having an exterior surface, said core rotatably secured to said axle, said core comprising:

a plurality of discrete radio frequency electrically conductive discharge points for applying the radio frequency electrical current to a plurality of discrete tissue locations, said radio frequency electrically conductive discharge points disposed on protrusions on said exterior surface and electrically connected to the active lead;

an electrically conductive reception member for receiving and returning at least a portion of the radio frequency electrical current discharged from said radio frequency electrically conductive discharge points, said electrically conductive reception member disposed on said exterior surface and electrically connected to the return lead; and an insulator disposed between said radio frequency electrically conductive discharge points and said electrically conductive reception member.

26. An apparatus connectable to an electrosurgical generator for facilitating diathermy of tissue with a radio frequency electrical current from the electrosurgical generator, comprising:

a core having an exterior surface;

a plurality of discrete radio frequency electrically conductive discharge points for applying the radio frequency electrical current to a plurality of discrete tissue locations, said radio frequency electrically conductive discharge points disposed on protrusions on said exterior surface of said core; and a positioning means disposed adjacent to said core for positioning said radio frequency electrically conductive discharge points relative to the tissue to facilitate diathermy, said positioning means comprising an active lead which is electrically connected to said radio frequency electrically conductive discharge points and which is electrically connectable to the electrosurgical generator, said core being rotatably secured to said positioning means such that successive pluralities of said radio frequency electrically conductive discharge points rotate into electrical contact with the tissue if an initial plurality of said radio frequency electrically conductive discharge points is placed in frictional engagement with the tissue and said positioning means is manipulated to roll said core along the tissue.

27. An apparatus connectable to an electrosurgical generator for facilitating diathermy of tissue with a radio frequency electrical current from the electrosurgical generator, comprising:

a core having an exterior surface;

a plurality of discrete radio frequency electrically conductive discharge points for applying the radio frequency electrical current to a plurality of discrete tissue locations, said radio frequency electrically conductive discharge points disposed on protrusions on said exterior surface of said core;

a positioning means disposed adjacent to said core for positioning said radio frequency electrically conductive discharge points relative to the tissue to facilitate diathermy, said positioning means comprising an active lead which is electrically connected to said radio frequency electrically conductive discharge points and which is electrically connectable to the electrosurgical generator, said core being rotatably secured to said positioning means; and an insulating layer that covers at least a portion of said exterior surface of said core, said insulating layer having perforations aligned with at least a portion of said radio frequency electrically conductive discharge points.

28. An apparatus connectable to an electrosurgical generator for facilitating diathermy of tissue with a radio frequency electrical current from the electrosurgical generator, comprising:

a core having an exterior surface;

a plurality of discrete radio frequency electrically conductive discharge points for applying the radio frequency electrical current to a plurality of discrete tissue locations, said radio frequency electrically conductive discharge points disposed on protrusions on said exterior surface of said core; and a positioning means disposed adjacent to said core for positioning said radio frequency electrically conductive discharge points relative to the tissue to facilitate diathermy, said positioning means comprising an active lead which is electrically connected to said radio frequency electrically conductive discharge points and which is electrically connectable to the electrosurgical generator, said positioning means comprising:

a shaft having a longitudinal axis; and an axle connected to said shaft and angled away from the longitudinal axis of said shaft, said core being rotatably secured upon said axle.

29. A bipolar apparatus connectable to an electrosurgical generator having an active lead and a return lead, the bipolar apparatus for facilitating diathermy by the application to tissue of a radio frequency electrical current emanating from the active lead of the electrosurgical generator, the bipolar apparatus comprising:

a core having an exterior surface, comprising:

a plurality of discrete radio frequency electrically conductive discharge points for applying the radio frequency electrical current to a plurality of discrete tissue locations, said radio frequency electrically conductive discharge points disposed on protrusions on said exterior surface and electrically connectable to the active lead of the electrosurgical generator;

an electrically conductive reception member for receiving and returning at least a portion of the radio frequency electrical current discharged from said radio frequency electrically conductive discharge points, said electrically conductive reception member disposed on said exterior surface and electrically connected to the return lead; and an insulator disposed between and electrically insulating said radio frequency electrically conductive discharge points from said electrically conductive reception member; and a positioning means disposed adjacent to said core, for positioning said exterior surface of said core relative to the tissue, said positioning means comprising a positioning means active lead which is electrically connected to said radio frequency electrically conductive discharge points and which is electrically connectable to the active lead of the electrosurgical generator, said positioning means comprising:

a shaft having a longitudinal axis; and an axle connected to said shaft and angled away from the longitudinal axis of said shaft, said core being rotatably secured upon said axle.

* * * * *